United States Patent [19]

Pedersen

[11] 4,115,375

[45] Sep. 19, 1978

[54] METHOD OF ISOLATION AND RECOVERY OF PROTEIN HORMONES, DERIVING FROM PITUITARY TISSUES USING POLYETHYLENE GLYCOL

[75] Inventor: Erik Pedersen, Ølstykke, Denmark

[73] Assignee: Nordisk Insulinlaboratorium, Gentofte, Denmark

[21] Appl. No.: 819,019

[22] Filed: Jul. 25, 1977

[30] Foreign Application Priority Data

Jul. 30, 1976 [DK] Denmark .............................. 3468/76

[51] Int. Cl.$^2$ ...................... A61K 35/46; C07G 7/026
[52] U.S. Cl. ...................... 260/112 R; 260/112.5 LH; 260/112.5 R; 424/108; 424/109
[58] Field of Search ............................. 424/109, 108; 260/112 R, 112.5 R

[56] References Cited

U.S. PATENT DOCUMENTS

| 3,415,804 | 12/1968 | Polson | 260/112 R |
| 3,763,135 | 10/1973 | Shanbrom et al. | 260/112 B |
| 3,808,189 | 4/1974 | Breuer | 260/112 B |

FOREIGN PATENT DOCUMENTS

| 128,054 | 7/1974 | Denmark. |
| 119,626 | 6/1971 | Denmark. |
| 127,676 | 6/1974 | Denmark. |
| 133,292 | 4/1976 | Denmark. |
| 2,515,666 | 10/1975 | Fed. Rep. of Germany. |
| 1,199,924 | 9/1965 | Fed. Rep. of Germany. |

*Primary Examiner*—Howard E. Schain
*Attorney, Agent, or Firm*—Lester Horwitz

[57] ABSTRACT

Protein hormones are fractionated and isolated from extracts of pituitary glands or tissues. Increased yield and purity of the growth hormone is obtained by using controlled amounts of polyethylene glycol as precipitating agent at pH = 4–6, preferably 4.5–5.0 and separating the precipitated fractions.

3 Claims, No Drawings

METHOD OF ISOLATION AND RECOVERY OF PROTEIN HORMONES, DERIVING FROM PITUITARY TISSUES USING POLYETHYLENE GLYCOL

The present invention relates to a method of isolation and recovery of protein hormones, deriving from pituitary tissues, by which an aqueous extract containing the protein hormones is subjected to fractionated precipitation with a precipitating agent.

It is particularly the object of the invention to isolate the pure growth hormone from extracts of pituitary tissues.

It is another object of the invention to provide a method by which the growth hormone may be selectively isolated from other protein hormones and impurities and thereby obtained in particularly pure condition and in high yield.

It is finally the object of the invention to provide a simplified process by which the growth hormone and other protein hormones from pituitary tissues are isolated and recovered.

It is known to isolate growth hormone by extraction of pituitary tissues and precipitation of the growth hormone from the extract by means of a precipitating agent.

Examples of publications describing processes for the recovery of human growth hormone are:

(1) Biochemica et biophysica Acta 1963, 74, pages 525–531, and
(2) Acta Endocrinologica 1971, 66, pages 478–490.

A method of separating mixtures of pituitary hormones is mentioned in Swiss Pat. No. 230,807. US Pat. Nos. 3,415,804, 3,652,530, 3,763,135 and 3,808,189 teach methods of fractionation of proteins by using polyethylene glycol as precipitating agent. However, it has been impossible to predict herefrom that polyethylene glycol is suitable for fractionation of pituitary hormones or for selective precipitation of the growth hormone under controlled conditions. The application of certain block copolymers is disclosed by Danish Pat. application No. 3321/74.

In the prior art processes for recovery of human growth hormone the highest yields are obtained with deep-frozen pituitary glands as starting material and by using lenient extraction and precipitation conditions. It is typical to proceed as follows:

(1) deep-frozen pituitary glands are extracted with a neutral or basic buffer,
(2) the extract is precipitated with a precipitating agent and/or by adjusting the pH-value at 4.8,
(3) the precipitate is extracted with a neutral or acid buffer,
(4) the extract is further purified by repeated precipitations and/or column chromatography, for instance gel filtration on Sephadex Gloo.

As precipitating agent in the above step 2 was previously used partly ammonium sulphate which, however, gives an impure end product, partly acetone which denatures the proteins to such a degree that they become soluble with difficulty in the subsequent extractions, resulting in poor yield.

The quality of the growth hormone is examined by using i.a. the following methods:
Biological activity (Tibia test)
Immunological activity (Radial immunodiffusion or Radio immunoassay)
Gel filtration (examination for polymers)
Electrophoresis in polyacrylamide gel (PAGE) (examination for foreign proteins).

A pure growth hormone is characterized by 1) an activity of more than two international units for each mg of protein, 2) more than 90% is available in monomeric form, 3) by PAGE of 100 μ there may only, after protein colouring, be demonstrated bands corresponding to growth hormone or growth hormone and 1-2 desamido forms hereof.

The method according to the invention is specific in that the aqueous extract from pituitary tissues is precipitated with one or more portions of polyethylene glycol at a pH-value of from 4 to 6, the amount of polyethylene glycol being so adjusted that the desired protein hormone or hormones are isolated in fractions, after which the fractions are processed in a manner known per se to isolate the protein hormones in purified condition.

By performing the precipitate in this way a pure product in high yield is obtained. For example, polyethylene glycol (PEG) acts more selectively as precipitating agent than ammonium sulphate. Thereby the pituitary hormones, especially the growth hormone, are obtained in purer condition. Moreover, the denaturation caused by acetone is avoided, resulting in a very high yield.

The method according to the invention is not confined to the use of primary pituitary extracts, but is also applicable to the isolation of peptide and protein hormones from for instance culture media from pituitary tissue cultures.

According to the invention it is preferred to conduct the precipitation with polyethylene glycol at a pH-value of from 4.5 to 5.0 which is the optimum value. Particularly good results are obtained at a pH-value of about 4.8.

The polyethylene glycol employed as precipitating agent has, according to the invention, a molecular weight preferably of from 3000 to 6000. However, the method may also be carried out with polyethylene of higher molecular weight than 6000 or lower molecular weight than 3000.

To separate and isolate the most important pituitary hormones, the method according to the invention may expediently be carried out by increasing the concentration of polyethylene glycol in the extract stepwise from 0 to 30% (W/V).

By filtering off the precipitate formed after each admixture an effective separation of the individual pituitary hormones is achieved. The fractions may then be processed separately to obtain the pure hormones.

According to a preferred embodiment of the invention by which the growth hormone is recovered it is expedient to isolate the fractions precipitated from the extract when the extract contains from 10 to 14% (W/V) polyethylene glycol.

This produces a high yield of precipitated growth hormone which can be purified in a manner known per se.

As starting material in the method described may be used any known extract of pituitary tissue or tissue cultures containing pituitary hormones. The extract may be prepared in a manner known per se, such as by mincing, chopping or otherwise comminution of pituitary glands and extraction with aqueous buffer solutions. A suitable extracting agent is an aqueous phosphate buffer having a pH-value of 8-9, such as 8.7.

Other buffers at higher or lower pH-value may be used instead.

It is expedient to add PEG to the filtered extract at a pH-value of 8–9, after which the pH-value is reduced to form 4.5 to 5.0, for instance 4.8, by addition of an acid, such as hydrochloric acid, sulphuric acid, phosphoric acid or acetic acid. It is also possible, however, to adjust the pH-value at from 4.5 to 5.0 first and then add PEG. If desired, the pH adjustment can be effected at the same time as the addition of PEG.

The amount of PEG depends on the pituitary hormone which it is desired to precipitate, and a stepwise admixture is effected when it is desirable to separate the maximum number of pituitary hormones. For example, the procedure may be initiated by an addition of PEG of about 10% and the mixture is filtered, whereafter the pH-value is adjusted at, for example, 4.8. After filtration, if desired, PEG is further admixed in one or more additions to obtain about 14% PEG. The resulting fractions contain growth hormone in high yield. Upon further additions other fractions are precipitated, for instance containing the pituitary hormones FSH and LH.

The precipitated fractions are processed in a manner known per se. The precipitate may for instance be isolated by centrifuging, after which it is re-dissolved in a buffer, such as at pH = 6.5–8, for example pH = 7.0. Thereafter precipitation is effected with saturated ammonium sulphate solution. The resulting precipitate is separated by centrifuging and re-dissolved in a buffer which is subjected to chromatography on a column containing a molecular sieve or an acid or basic ion exchanger resin. By the chromatography the fractions containing the pure pituitary hormones, such as the growth hormone, are isolated.

The method according to the invention will be illustrated in greater detail below by means of some examples.

EXAMPLE 1

24 deep-frozen human piutitary glands are homogenized while adding 100 ml of a buffer (I) composed as follows: 1.8% disodium hydrogen phosphate in water, admixed with 1N sodium hydroxide to pH = 8.7. The mixture is centrifuged. To 90 ml of supernatant liquid is added 24 ml of an aqueous solution of 50 g of polyethylene glycol 6000 in 100 ml solution. After stirring for 30 minutes the mixture is centrifuged and the pH-value of the supernatant is adjusted at 4.8 by means of 1N of hydrochloric acid. After centrifuging the precipitate is extracted with 60 ml of a buffer (II) composed as follows: 1.4% disodium hydrogen phosphate, 4.9% monosodium dihydrogen phosphate, admixed with 1N sodium hydroxide to pH = 7.0. After stirring for 1 hour the mixture is centrifuged and the supernatant is admixed with 60 ml of saturated ammonium sulphate solution. The mixture is centrifuged again and the precipitate is dissolved in 25 ml of a solution (III) composed as follows: 2% aminoacetic acid and 0.25% sodium hydrogen carbonate. This solution is applied to a column, 79 cm long and 2.5 cm in diameter, containing Sephadex G100, equilibrated with solution III. The column is eluated with solution III, the fractions corresponding to the elution volume of 260—320 ml are collected. The collected fractions contain 260 units of human growth hormone, with a specific activity of 2.2 units for each mg of protein. Electrophoresis on polyacrylamide gel of 100 $\mu$ protein shows only 3 bands, corresponding to growth hormone and the desamido forms.

EXAMPLE 2

250 deep-frozen human pituitary glands are extracted as described in example 1 with 1500 ml of buffer I. To the supernatant is added 460 ml of a solution consisting of 230 g polyethylene glycol 3000 and 270 ml water. After stirring for 20 minutes and centrifuging, the pH-value of the supernatant is adjusted at 4.9 with 1N of hydrochloric acid. After stirring for 20 minutes and centrifuging, the precipitate is extracted as stated in example 1 with 1000 ml of buffer II. After stirring overnight and centrifuging 1000 ml of saturated ammonium sulphate solution is added to the supernatant. The mixture is centrifuged again, and the precipitate is dissolved in 300 ml of a solution of 126 g urea in 207 ml buffer III (see example 1). The solution is applied to a column, 100 cm long and 11.4 in diameter, containing Sephadex G100, equilibrated with buffer III. The column is eluated with buffer III. Fractions corresponding to the elution volume for growth hormone are collected. The collected fractions contain 2900 units of human growth hormone, with a specific activity of 2.6 units for each mg of protein. Electrophoresis on polyacrylamide gel of 100 $\mu$ shows only 2 bands, corresponding to growth hormone and a desamido form.

EXAMPLE 3

500 deep-frozen human pituitary glands are extracted as stated in example 1 with 2000 ml of buffer I. After centrifuging the pH-value is adjusted at 4.8. The mixture is centrifuged. The precipitate is processed into pure growth hormone by extraction with buffer II, precipitation, re-dissolution in buffer III and column chromatography as described in example 2. There is obtained 3400 units of growth hormone with a specific activity of 2.7 units for each mg of protein.

The supernatant is admixed with 650 ml solution, consisting of 325 g polyethylene glycol 3000 and 380 ml water. The mixture is centrifuged. The precipitate is subjected to extraction with buffer II, precipitaion with ammonium sulphate, re-dissolution, buffer III and column chromatography as described in example 2. The collected growth hormone-containing fractions contain 4230 units of growth hormone with a specific activity of 2.6 units for each mg of protein.

The total yield from 500 pituitary glands was thus 7630 units.

EXAMPLE 4

500 deep-frozen human pituitary glands are extracted as described in example 1 with 2000 ml of buffer I. After centrifuging the pH is adjusted at 4.8. The mixture is centrifuged again. The supernatant is admixed with 1300 ml solution, consisting of 650 g polyethylene glycol 3000 and 760 ml water. The mixture is centrifuged. The precipitate is subjected to extraction with buffer II and precipitaion with ammonium sulphate as described in example 2. The mixture is centrifuged. To 2000 ml of the supernatant is added 1000 ml solution consisting of 500 g polyethylene glycol 3000 and 585 ml water. After stirring for 1 hour the mixture is centrifuged. The precipitate contains the pituitary hormones FSH and LH.

EXAMPLE 5

100 ml culture medium from tissue culture of the anterior pituitary, containing 5 units of growth hormone, is concentrated by ultra filtration to 1 ml. There is added 0.5 ml of an aqueous solution containing 0.5 g polyethylene glycol 6000 for each ml. The pH-value of the solution is adjusted at 4.8. The precipitate is separated, dissolved in 0.5 ml water and applied to a column, 63 cm long and 0.9 cm in diameter, containing Sephadex Gloo, equilibrated with buffer III. Eluation is effected with buffer III. The fractions containing growth hormone are collected. The collected fractions contain 1.0 units of human growth hormone with a specific activity of 2.0 units for each mg of protein.

What I claim is:

1. A method of isolating and recovering the growth hormone and a fraction containing the hormones FSH ad LH from pituitary tissues, comprising the steps of
   (a) extracting tissues from pituitary glands with an aqueous alkaline buffer,
   (b) admixing the extract with an aqueous solution of polyethylene glycol (PEG) in an amount corresponding to 10-14% PEG by weight per volume before or after adjusting the pH to from 4.5 to 5.0,
   (c) isolating the precipitated growth hormone,
   (d) admixing the supernatant from the previous step with an aqueous solution of polyethylene glycol and
   (e) isolating a mixture of the hormones FSH and LH precipitated in step d).

2. Method according to claim 1, wherein the polyethylene glycol used as precipitating agent has a molecular weight of from 3000 to 6000.

3. Method accordng to claim 1, wherein the concentration of polyethylene glycol in the extract is increased stepwise from 0 to 30% (W/V).

* * * * *